United States Patent
Kubota et al.

(10) Patent No.: US 11,058,718 B2
(45) Date of Patent: Jul. 13, 2021

(54) METHOD FOR TREATING NON-ALCOHOLIC STEATOHEPATITIS (NASH) WITH THE COMBINATION OF POLAPREZINC AND SODIUM SELENITE

(71) Applicant: Medico Consl Co., Ltd., Osaka (JP)

(72) Inventors: Satoru Kubota, Osaka (JP); Toru Kono, Hokkaido (JP)

(73) Assignee: MEDICO CONSL CO., LTD., Suita (JP)

( * ) Notice: Subject to any disclaimer, the term of this patent is extended or adjusted under 35 U.S.C. 154(b) by 0 days.

(21) Appl. No.: 16/892,728

(22) Filed: Jun. 4, 2020

(65) Prior Publication Data

US 2020/0405754 A1    Dec. 31, 2020

Related U.S. Application Data

(63) Continuation-in-part of application No. 16/473,888, filed on Jun. 26, 2019, now abandoned.

(51) Int. Cl.
  *A61K 33/30*   (2006.01)
  *A61P 1/16*    (2006.01)
  *A61K 33/04*   (2006.01)

(52) U.S. Cl.
  CPC ............. *A61K 33/30* (2013.01); *A61K 33/04* (2013.01); *A61P 1/16* (2018.01)

(58) Field of Classification Search
  USPC ........................................................ 514/494
  See application file for complete search history.

(56) References Cited

PUBLICATIONS

Sugino (Polaprezinc attenuates liver fibrosis in a mouse model of non-alcoholic steatohepatitis, Journal of Gastroenterology and Hepatology 23, 2008, pp. 1909-1916).*

Ming Ding (Selenium Supplementation Decreases Hepatic Fibrosis in Mice After Chronic Carbon Tetrachloride Administration, Biol Trace Elem Res, 2010, 133(1), pp. 83-97).*

Japanese Notification of Reasons for Refusal mailed by Japanese Patent Office dated Jan. 27, 2020 in corresponding Japanese patent application No. 2019-516717.

Li, Tan et al., Vitamin E and Se interfere in cytochrome P4501A1 and lipid peroxidation in nonalcoholic fatty liver, World Chinese Journal of Digestology, Oct. 8, 2007, vol. 15, No. 28, ISSN:1009-3079, p. 2977-2982.

Japanese Decision of Refusal mailed by Japanese Patent Office dated Apr. 13, 2020 in corresponding Japanese patent application No. 2019-516717.

Chinese Notification of Reasons for Refusal mailed by Chinese Patent Office dated Nov. 11, 2020 in corresponding Chinese patent application No. 201780069336.5.

Haruko Sugino et al., Polaprezinc attenuates liver fibrosis in a mouse model of non-alcoholic steatohepatitis, Journal of Gastroenterology and Hepatology, vol. 23, p. 1909-1915.

Ma Na, Sodium selenite improves nonalcoholic fatty liver disease by reversing abnormal thyroid hormone transformation, Chinese excellent masters thesis collection (medical health science technology) issue02, p. 38.

Ashwani K. Signal et al., Antioxidants as therapeutic agents for liver disease, Liver International. 1432-1448.

* cited by examiner

*Primary Examiner* — Kathrien A Cruz

(74) *Attorney, Agent, or Firm* — IP Business Solutions, LLC

(57) ABSTRACT

Provided is a method for treating non-alcoholic steatohepatitis (NASH), the method includes administering to a subject in need thereof a therapeutically effective amount of a pharmaceutical composition and the pharmaceutical composition contains polaprezinc as zinc preparation and sodium selenite as selenium preparation.

1 Claim, 11 Drawing Sheets
(3 of 11 Drawing Sheet(s) Filed in Color)

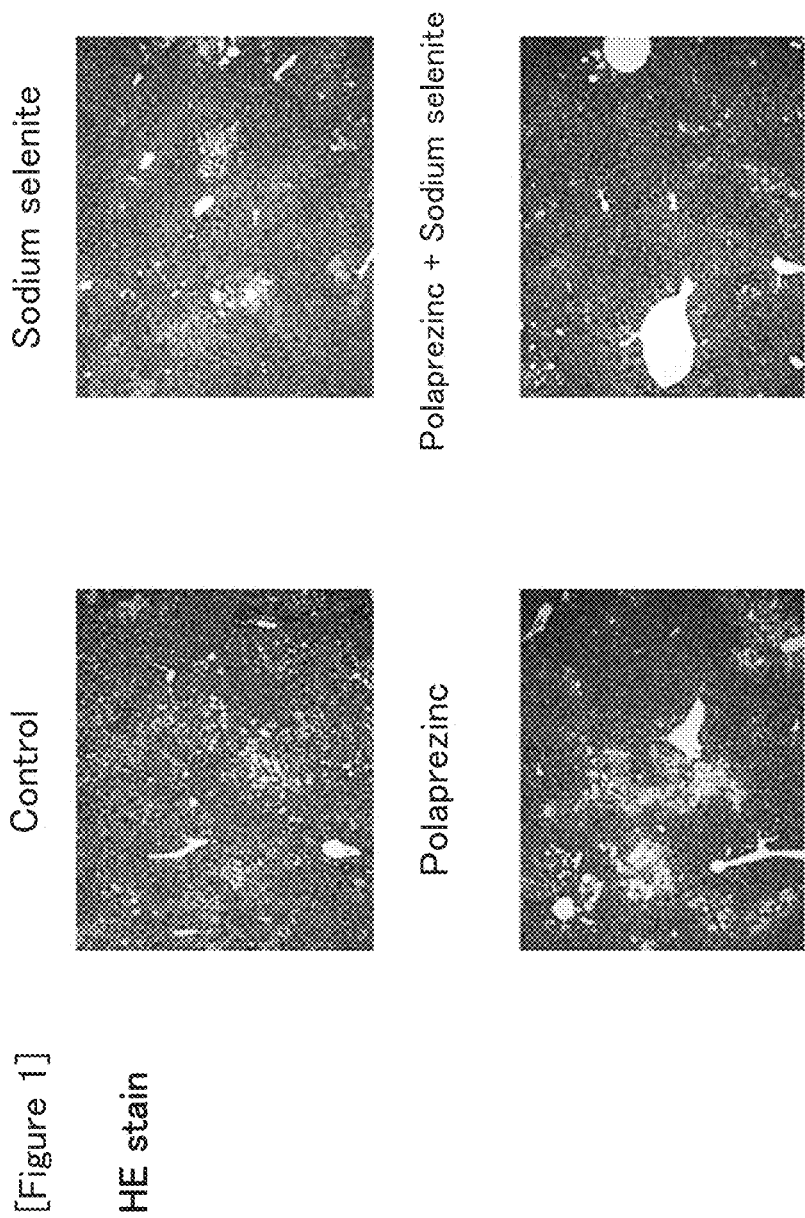
[Figure 1]
HE stain

[Figure 2-1]
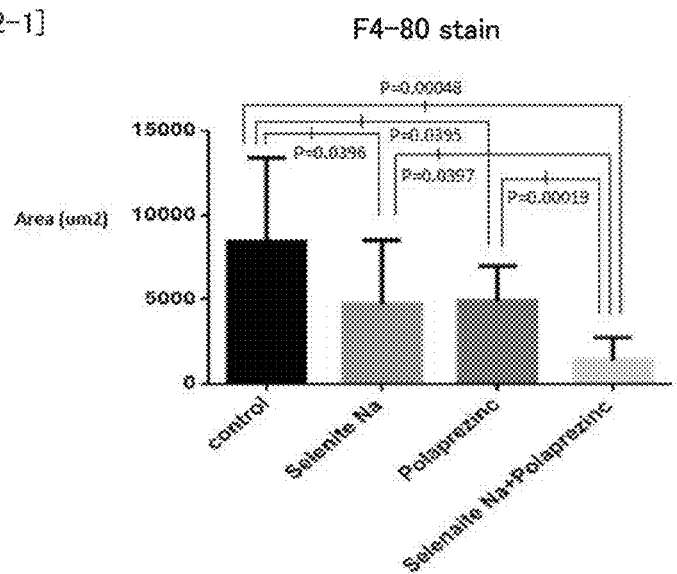

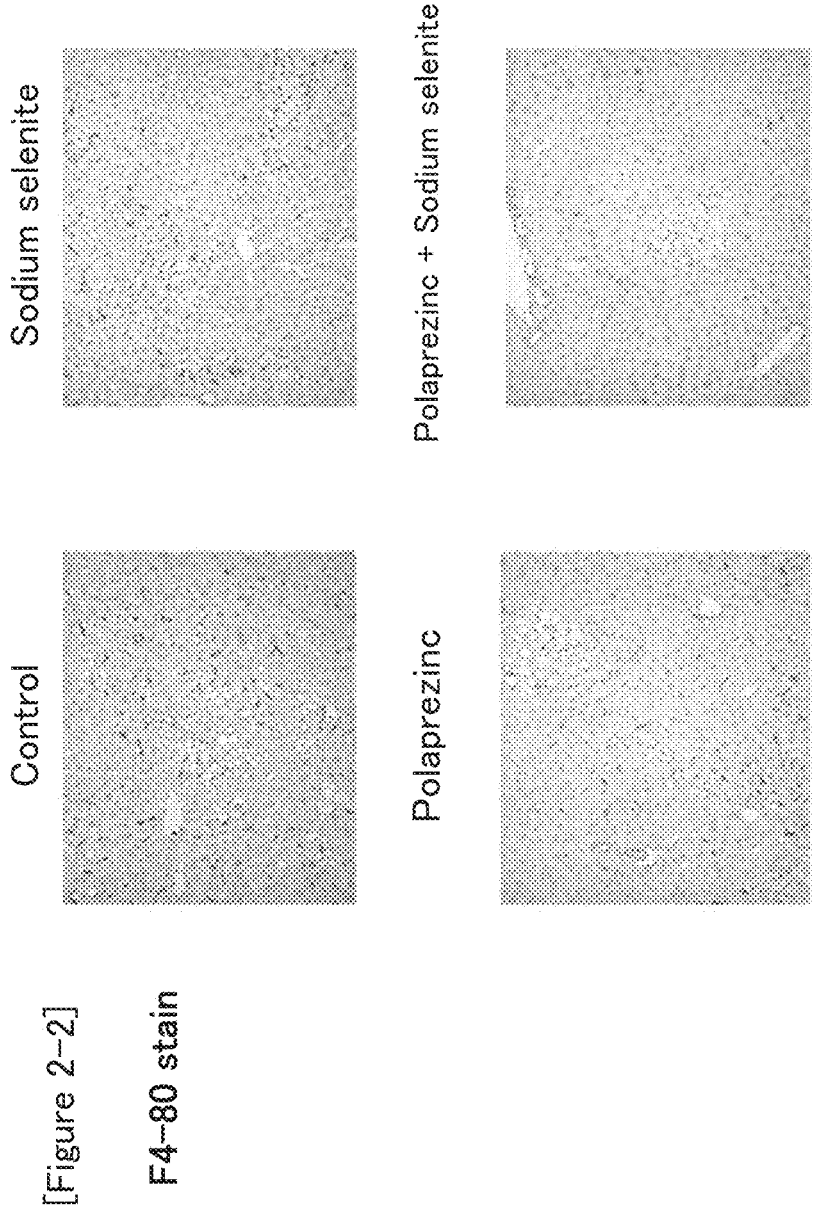
[Figure 2-2]
F4-80 stain

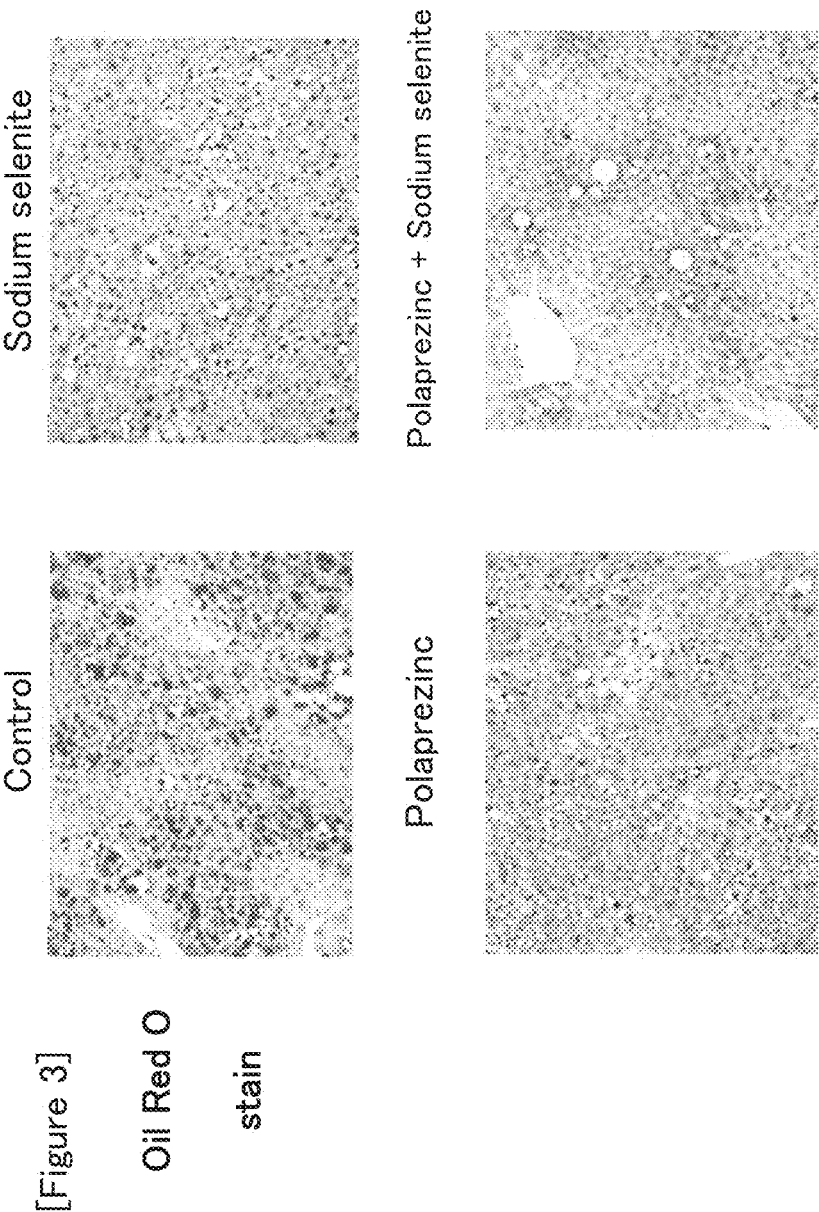
[Figure 3]
Oil Red O stain

[Figure 4]
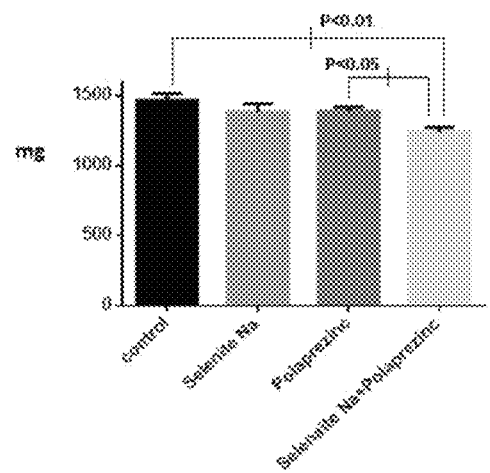
[Figure 5]
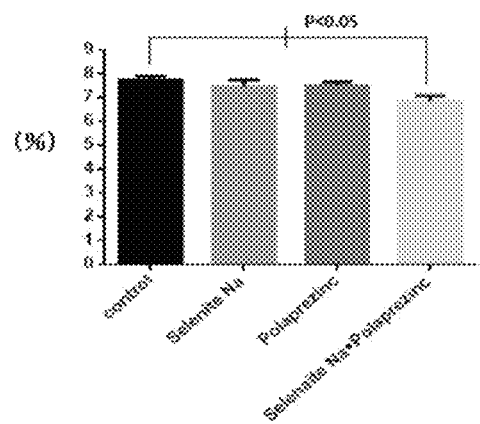

[Figure 6]
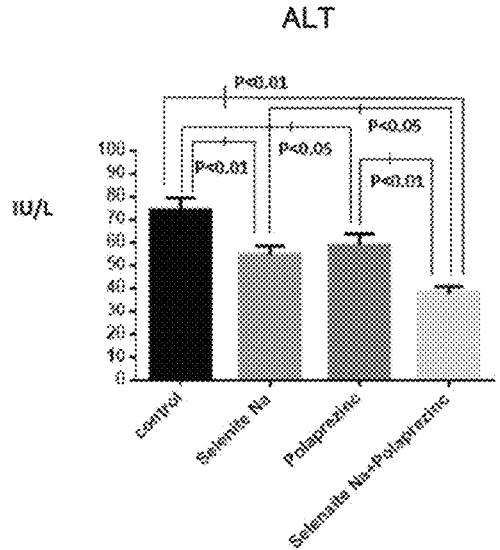
[Figure 7]
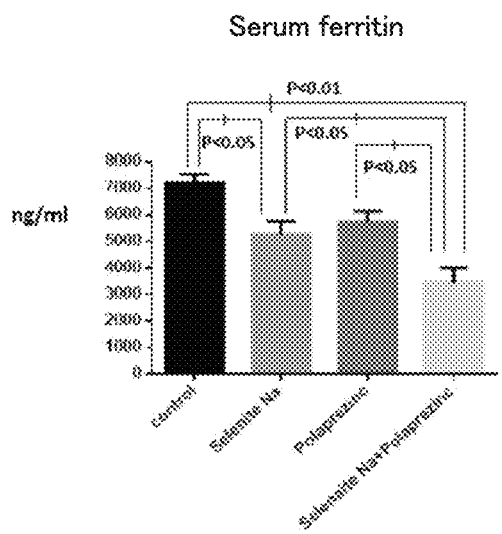

[Figure 8]
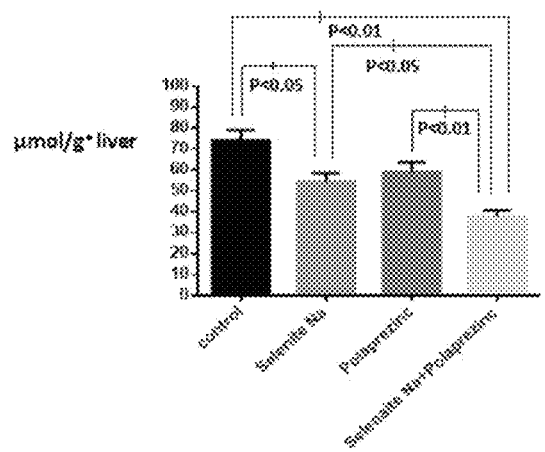
[Figure 9]
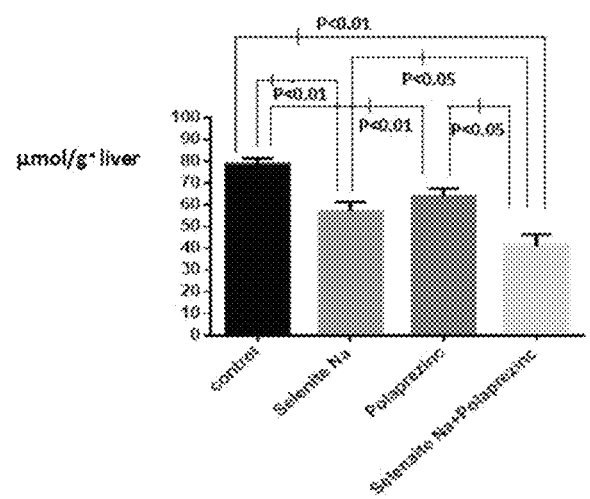

[Figure 10] MCP-1 (monocyte chemotactic protein-1)
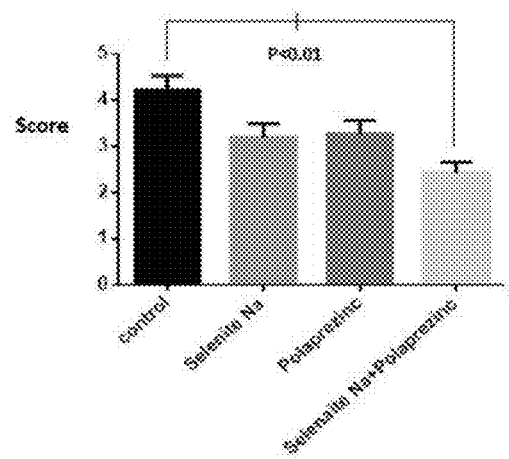
[Figure 11] TNF-alpha (tumor necrosis factor-alpha)
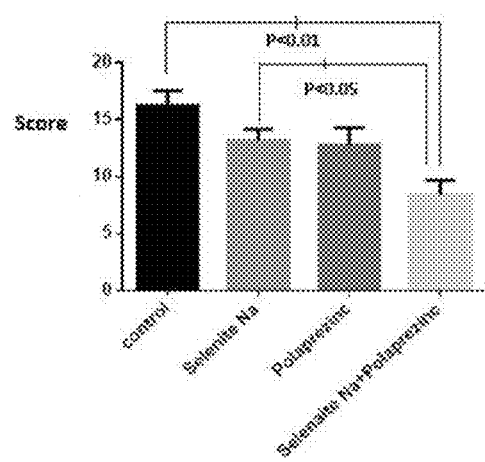

[Figure 12]
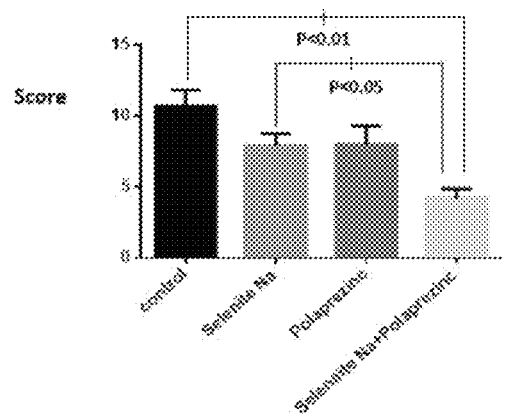
IFN-gamma (interferon-gamma)
[Figure 13]
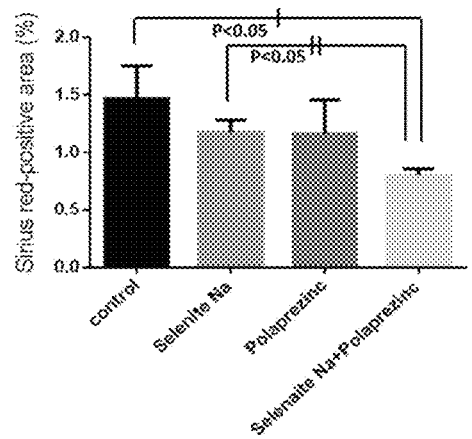
Percent of Fibrosis Area
(hepatic fibrosis area ratio)

[Figure 14]
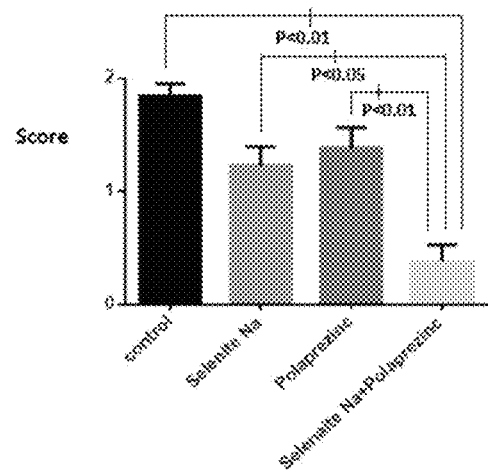
Hepatocyte Ballooning
(hepatic ballooning)
[Figure 15]
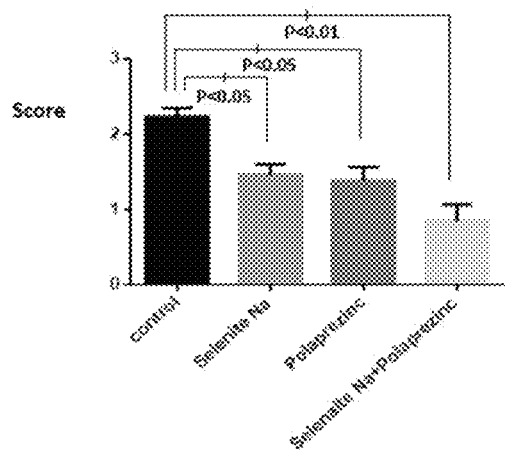
Lobular Inflammation
(hepatic lobular inflammation)

[Figure 16]
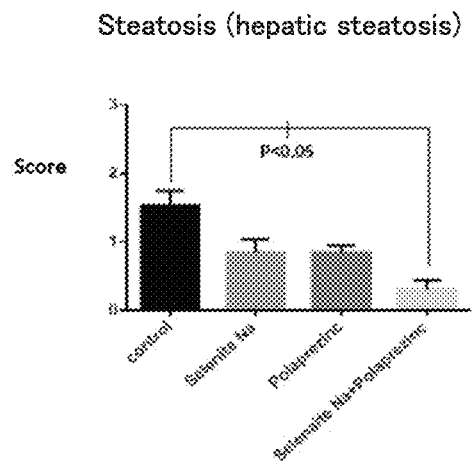
[Figure 17]
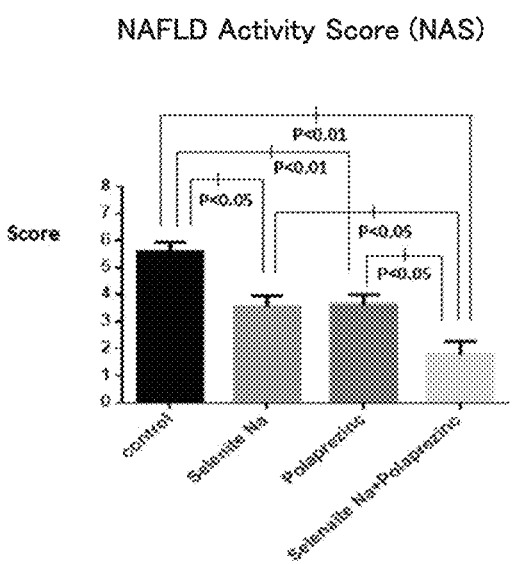

METHOD FOR TREATING NON-ALCOHOLIC STEATOHEPATITIS (NASH) WITH THE COMBINATION OF POLAPREZINC AND SODIUM SELENITE

This application is a continuation-in-part application of U.S. application Ser. No. 16/473,888, filed on Jun. 26, 2019, which claims the priority to International Patent Application No. PCT/JP2017/043898, filed on Nov. 30, 2017.

TECHNICAL FIELD

The present invention is related to a method of using a pharmaceutical combination drug and health food suitable for treatment and prevention of non-alcoholic fatty liver disease (NAFLD) and/or non-alcoholic steatohepatitis (NASH).

Further in detail, the present invention is related to a combination drug of zinc preparation, especially polaprezinc, and selenium preparation, especially sodium selenite for treating non-alcoholic fatty liver disease (NAFLD) and/or non-alcoholic steatohepatitis (NASH), and a combination drug of zinc preparation, especially polaprezinc, and selenium preparation, especially sodium selenite for treatment of diseases related or associated with non-alcoholic fatty liver disease (NAFLD) and/or non-alcoholic steatohepatitis (NASH). It may contain zinc preparation, especially polaprezinc, and selenium preparation, especially sodium selenite defined in the present specification and combine one kind or plural kinds of other active substances, and the pharmaceutical combination drug and health food for use in treatment and prevention of non-alcoholic fatty liver disease (NAFLD) and/or non-alcoholic steatohepatitis (NASH) is also attempted. It may be described as zinc preparation (polaprezinc) and selenium preparation (sodium selenite) hereafter in the present specification, but such description is an indication of typical examples of zinc preparation and selenium preparation.

BACKGROUND ART

Fatty liver not induced by alcohol advance from fatty liver degeneration to inflammatory steatohepatitis (NASH; non-alcoholic steatohepatitis) and progress to cirrhosis and hepatocellular carcinoma through hepatic fibrosis. Non-alcoholic steatohepatitis (NASH) is an advanced state of non-alcoholic fatty liver disease (NAFLD), and patients are estimated to be not less than one million people for NASH and 10 million people for NAFLD in Japan. In North America, 6 to 15% of the adults and in Europe, 3 to 15% of ditto is estimated to be non-alcoholic steatohepatitis (NASH). Therefore, a prevention and treatment measure is in urgent need. Now, as for the onset mechanism of non-alcoholic fatty liver disease (NAFLD) and/or non-alcoholic steatohepatitis (NASH), fatty liver degeneration is induced at first attributed to change inside and outside of the liver. It is considered that the inflammation promotes by the level of inflammatory cytokine elevating in response to this. Additionally, abnormal glucose metabolism attributed to obesity, diabetes and the like is deeply involved with the onset. For measures in relation to non-alcoholic fatty liver disease (NAFLD) and/or non-alcoholic steatohepatitis (NASH), diet therapy, exercise therapy, and weight management are the main coping methods, and while health foods and decisive therapeutic agents addressing prevention is not developed at present, the advent of health foods addressing prevention and safe and effective pharmaceuticals usable for a long term is being awaited.

Treatments for hepatitis, especially viral hepatitis type C, dramatically changed from treatments with interferons and antivirals by the advent of polymerase inhibitors which suppress viral growth by inhibiting protein involved in replication of hepatitis C virus and protease inhibitors inhibiting RNA synthesis of hepatitis C virus and the like, and the result that there are not less than 90% patients whose hepatitis viral load of the hepatitis C patient improved to not more than the measurement detection limit (SVR: sustained virological response) is reported.

Though therapeutic agents which improve the hepatitis viral load of the hepatitis C patient to not more than the measurement detection limit (SVR: sustained virological response) have been developed and are already in clinical applications, established therapeutic agents for non-alcoholic fatty liver disease (NAFLD) and/or non-alcoholic steatohepatitis (NASH) which hepatitis virus is not involved does not yet exist. For non-alcoholic fatty liver disease (NAFLD) and/or non-alcoholic steatohepatitis (NASH) rapidly increasing worldwide, development of therapeutic agents which suppress progress to cirrhosis, liver cancer, and improve liver function is being awaited.

In non-alcoholic fatty liver disease (NAFLD) and/or non-alcoholic steatohepatitis (NASH), hepatic fibrosis advance in 37%, and fibrosis easily advance when combined with diabetes and easily transits to cirrhosis with high BMI (nonpatent literature 1). Fibrosis do not necessarily advance in non-alcoholic fatty liver disease (NAFLD) and/or non-alcoholic steatohepatitis (NASH), but suppression of hepatic fibrosis becomes important to suppress severity. Furthermore, it is reported that approximately 5% progress to cirrhosis in non-alcoholic fatty liver disease (NAFLD) and/or non-alcoholic steatohepatitis (NASH) (nonpatent literature 2). For zinc preparation (polaprezinc), it is already shown that it suppresses hepatic fibrosis and is disclosed as Japanese Patent No. 4802470 (patent literature 1).

PRIOR ART LITERATURES

Nonpatent Literature 1

Adams L A et. al, "The histological course of nonalcoholic fatty liver disease: a longitudinal study of 103 patients with sequential liver biopsies.", J. Hepatology 2005.42(1): 132-138

Nonpatent Literature 2

Adams L A et. al, "The natural history of nonalcoholic fatty liver disease: a population-based cohort study", Gastroenterology 2005.129(1) 113-121

Patent Literature 1

Japanese Patent No. 4802470

Zinc preparation (polaprezinc) is known to be effective as a peptic ulcer therapeutic agent and is generally used in Japan and Republic of Korea. Zinc preparation (polaprezinc) used as a peptic ulcer therapeutic agent is known as L-carnosine zinc salt (patent literature 1).

Selenium preparation (sodium selenite) shows to suppress hepatic fibrosis (nonpatent literature 3).

Nonpatent Literature 3

Ming Ding et. al, "Selenium Supplementation Decreases Hepatic Fibrosis in Mice After Chronic Carbon Tetrachloride Administration", Biol Trace Elem Res 2010.133(1) 83-97

Selenium preparation (sodium selenite) is used overseas for the purpose of improving visual disturbance, neuropathy, myocardial damage, and hair change. Use as a medical therapeutic agent for the purpose of prevention and treatment of liver function is not authorized overseas, including Japan.

The features of non-alcoholic fatty liver disease (NAFLD) and/or non-alcoholic steatohepatitis (NASH) emerge as a tissue image of deposition of macrovesicular fat in the liver tissue, balloon-like hypertrophy (ballooning) of the hepatocyte fibrosis around the hepatocyte, infiltration of the inflammatory cell, and the like. NAS (NAFLD activity score) is used as an index of non-alcoholic fatty liver disease (NAFLD) and/or non-alcoholic steatohepatitis (NASH) activity, and is used as an overall evaluation of NAFLD. This puts three items of steatosis, inflammatory cell infiltration, ballooning degeneration into scores, and determines the activity according to full score 8 of NAS. It is a clinically applied method after being presented by Kleiner on 2005 (nonpatent literature 4).

Nonpatent Literature 4

Kleiner. D. E, et. al, "Design and Validation of a Histological Scoring System for Nonalcoholic Fatty Liver Disease", Hepatology 2005.41(6):1313-1321

Hepatic fibrosis-suppressing action is reported for zinc preparation (polaprezinc) and selenium preparation (sodium selenite) respectively, but improvement in the tissue image of deposition of macrovesicular fat in the liver tissue, balloon-like hypertrophy (ballooning) of the hepatocyte, infiltration of the inflammatory cell, and the like, which are the features of non-alcoholic fatty liver disease (NAFLD) and/or non-alcoholic steatohepatitis (NASH), and improvement effects using NAS (NAFLD activity score) are not ascertained. Since both have a strong active oxygen scavenging action, treatments for non-alcoholic fatty liver disease (NAFLD) and/or non-alcoholic steatohepatitis (NASH) using zinc preparation (polaprezinc) alone, selenium preparation (sodium selenite) alone, and the combination drug of zinc preparation (polaprezinc) and selenium preparation (sodium selenite) were performed and examined.

Zinc preparation (polaprezinc) alone and selenium preparation (sodium selenite) alone showed improvement compared to the control group, but both only to a level that nonalcoholic steatohepatitis (NAFLD) and/or nonalcoholic steatohepatitis (NASH) and normal hepatocytes were mixed equally and did not lead to amelioration of nonalcoholic fatty liver disease (NAFLD) and/or non-alcoholic steatohepatitis (NASH). The combination drug of zinc preparation (polaprezinc) and selenium preparation (sodium selenite) showed a NAS(NAFLD activity score) almost conceivable as a normal liver, and a significant improvement was recognized for non-alcoholic fatty liver disease (NAFLD) and/or non-alcoholic steatohepatitis (NASH) compared with the control group, zinc preparation (polaprezinc) alone and selenium preparation (sodium selenite) alone. Further, with regard to zinc preparation (polaprezinc), improvement effects limited to hepatic fibrosis in non-alcoholic fatty liver disease (NAFLD) and/or non-alcoholic steatohepatitis (NASH) have been reported (non-patent document 5). However, improvement of macrovesicular fat accumulation in liver tissue and balloon-like hypertrophy (ballooning) of the hepatocyte and cell inflammation infiltration characterized in non-alcoholic fatty liver disease (NAFLD) and/or non-alcoholic steatohepatitis (NASH) have not been confirmed by looking at improvement in histologic images and improvement action of NAS (NAFLD activity score) results. In addition, for non-alcoholic fatty liver disease (NAFLD), the additional improvement effect is examined with a group additionally administered with zinc preparation (polaprezinc) to drugs expected to improve liver function such as ursodeoxycholic acid and lipid-improving drugs and a non-administration group, but the result is suppression of hepatic fibrosis and suppression of inflammation (nonpatent literature 6), and improvement in deposition of macrovesicular fat in the liver tissue, balloon-like hypertrophy (ballooning) of the hepatocyte, and NAS (NAFLD activity score) are not shown. Furthermore, non-alcoholic steatohepatitis (NASH) was observed after pancreatoduodenectomy, and diarrhea and liver function normalized after administration of a large amount of pancreatic enzymes and zinc preparation (polaprezinc). Subsequent serial administration resulted in normalization within the image (nonpatent literature 7). This shows the effect of combining a large amount of pancreatic enzymes and zinc preparation (polaprezinc). The effect of zinc preparation (polaprezinc) on non-alcoholic fatty liver disease (NAFLD) and/or non-alcoholic steatohepatitis (NASH) is not confirmed.

Nonpatent Literature 5

Sugino. H et. al, "Polaprezinc attenuates liver fibrosis in a mouse model of non-alcoholic steatohepatitis", J Gastroenterol Hepatol 2008.23(12) 1909-1916

Nonpatent Literature 6

Takamatsu Seigo et. al, "Beneficial effects of zinc supplement in NAFLD treatment", Therapeutic Research 2011.32 (7) 967-973

Nonpatent Literature 7

Y Murata et. al, "Nonalcoholic steatohepatitis (NASH) after pancreaticoduodenectomy: association of pancreatic exocrine deficiency and infection", Clin J Gastroenterol 2011.4.242-248

SUMMARY OF INVENTION

Problem to be Solved by the Invention

The purpose of the present invention is to provide medicine and health food suitable for treatment and prevention of non-alcoholic fatty liver disease (NAFLD) and/or non-alcoholic steatohepatitis (NASH), and/or hepatic fatty degeneration which are not involved with hepatitis virus.

Means for Solving the Problem

The present invention provides a combination drug suitable for treatment and prevention of non-alcoholic fatty liver disease (NAFLD) and/or non-alcoholic steatohepatitis (NASH), and/or hepatic fatty degeneration, wherein the active ingredients are zinc preparation and selenium preparation. Namely, the pharmaceutical combination drug and health food suitable for treatment and prevention of non-alcoholic fatty liver disease (NAFLD) and/or non-alcoholic steatohepatitis (NASH), and/or hepatic fatty degeneration of the present invention is a combination drug of zinc preparation and selenium preparation.

In particular, but are not limited to, the combination drug of polaprezinc as zinc preparation and sodium selenite as selenium preparation is desirable in the present invention. Polaprezinc is L-carnosine zinc salt. Thus, the present invention related to a method for treating non-alcoholic steatohepatitis (NASH) and the method includes administering to a subject in need thereof a therapeutically effective amount of a pharmaceutical composition. Specifically, the pharmaceutical composition contains polaprezinc as zinc preparation and sodium selenite as selenium preparation.

As particular aspects of the present invention, oral administration is preferable, and 0.015 g to 0.25 g per day per adult as the zinc content of zinc preparation and 10 μg to 450 μg per day per adult for the compounding amount as the selenium content of selenium preparation is preferable. As the zinc content of zinc preparation, when it is less than 0.015 g per day per adult, it is insufficient for the recommended dietary intake by the Ministry of Health, Labor and Welfare and the dosage is too less for prevention and treatment of diseases, and when it is more than 0.25 g, safety of long term administration is concerned. There is a point that the daily maximum dose of zinc in zinc acetate, which is one of a zinc preparation authorized as a pharmaceutical, is set to 0.25 g. Furthermore, for the compounding amount as the selenium content of selenium preparation, when it is less than 10 μg per day per adult, it is insufficient for the recommended dietary intake by the Ministry of Health, Labor and Welfare and the dosage is too less for prevention and treatment of diseases, and when it is more than 450 μg, since it exceeds the dietary intake upper limit by the Ministry of Health, Labor and Welfare, safety was considered.

The present invention is related to a combination drug containing zinc preparation and selenium preparation as active ingredients, but at least one or more substances of vitamin C, vitamin E, Rhodiola sacra which is an alpine plant, metformin, which improves insulin resistance, pioglitazone, DPP-4 inhibitors, EPA (eicosapentaenoic acid) which has an anti-oxidant action, bezafibrate which improves hyperlipidemia, HMG-CoA reductase inhibitors, hypercholesterolemia improving agents, angiotensin II receptor antagonists, pentoxifylline which has an anti TNF-alpha action may be combined with this.

Effects of the Invention

According to the present invention, it is possible to recover normal liver and suppress progress to cirrhosis, liver cancer by improving non-alcoholic fatty liver disease (NAFLD) and/or non-alcoholic steatohepatitis (NASH).

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1: A figure showing the HE stained tissue image of the four groups.

FIG. 2-1: A figure showing the F4/80 (macrophage) stained tissue image of the four groups.

FIG. 2-2: A figure showing the F4/80 (macrophage) stained tissue image of the four groups.

FIG. 3: A figure showing the Oil-Red-O stained (intracellular lipid droplets) tissue image of the four groups.

FIG. 4: A figure showing liver weight.

FIG. 5: A figure showing the data of the weight ratio of liver to body.

FIG. 6: A figure showing the data of ALT.

FIG. 7: A figure showing the data of serum ferritin.

FIG. 8: A figure showing the data of MDA (malondialdehyde).

FIG. 9: A figure showing the data of hepatic TG (hepatic triglyceride).

FIG. 10: A figure showing the data of MCP-1 (monocyte traveling protein-1).

FIG. 11: A figure showing the data of TNF-alpha (tumor necrosis factor-alpha).

FIG. 12: A figure showing the data of IFN-gamma (interferon-gamma).

FIG. 13: A figure showing the data of hepatic fibrosis area ratio.

FIG. 14: A figure showing the data of hepatic ballooning.

FIG. 15: A figure showing the data of lobular inflammation (lobular inflammation).

FIG. 16: A figure showing the data of steatosis (steatosis).

FIG. 17: A figure showing the data of NAS (NAFLD activity score).

EMBODIMENT OF THE INVENTION

An internationally prized and recognized STAM (registered trademark) mouse was used for the research model of non-alcoholic fatty liver disease (NAFLD) and/or non-alcoholic steatohepatitis (NASH). A STAM (registered trademark) mouse is an animal model of non-alcoholic steatohepatitis prepared by administrating inflammation inducer of the pancreas (patent literature 2) which Stelic Institute & Co. developed and is publically informed as patentee, and many research reports using this animal model has already been made domestic and overseas.

Patent Literature 2

Japanese Patent No. 5337245

The active ingredient zinc preparation (polaprezinc) of the present invention can be obtained by the method of Japanese Examined Patent Application Publication No. H3-5367. The selenium preparation (sodium selenite) is obtained by synthesizing selenious acid and sodium hydroxide. Sodium selenite is already used overseas for the purpose of improving severe visual disturbance, neuropathy, myocardial damage, and hair change caused by selenium deficiency. Furthermore, it is used for treatment of Keshan disease caused by selenium deficiency in China. It is extremely important that an effective combination drug for treatments of illness without an established therapeutic agent was obtained using known two ingredients, zinc preparation (polaprezinc) and selenium preparation (sodium selenite).

An oral administration preparation is preferable for the pharmaceutical of the present invention. Especially, tablets, capsules, powders, syrups, and the like are preferable.

Among the manufacture of the combination drug of zinc preparation (polaprezinc) and selenium preparation (sodium selenite), as zinc preparation (polaprezinc), distilled water for injection, purified water, carboxymethylcellulose, mannitol, sucrose, corn starch, microcrystalline cellulose, lactitol, Cellulose derivatives, gum arabic, gum tragacanth, gelatin, polysorbate 80, talc, magnesium stearate, water, ethanol, white petrolatum, glycerin, fat, fatty oil, glycol, higher alcohol such as stearyl alcohol, plastibase, paraffin, beeswax, Polyoxyethylene hydrogenated castor oil, saccharin, pine syrup and the like can be appropriately selected and combined. As the selenium preparation (sodium selenite), it can be obtained by synthesizing selenious acid and sodium hydroxide.

For the zinc content of zinc preparation as the combination ingredient, 0.015 g to 0.25 g per day per adult as the zinc content of zinc preparation is preferable, varying depending on age, body weight, pathological condition, therapeutic effect, time of administration, number of administration, period of administration, method of administration. Similarly, for the compounding amount as the selenium content of selenium preparation, 10 μg to 450 μg per day per adult for the compounding amount as the selenium content of selenium preparation is preferable, varying depending on age, body weight, pathological condition, therapeutic effect, time of administration, number of administration, period of administration, method of administration, and it is preferable to administrate this combination drug dividedly in one to four times a day.

Example

The present invention will be described in detail by giving examples, but the present invention is not limited to the examples.

Example

The NASH model mice were assigned to four groups (eight mice per group) by body weight stratification random sampling method so that the average body weight is equal. The four groups are the zinc preparation (polaprezinc)+selenium preparation (sodium selenite) group, zinc preparation (polaprezinc) alone group, selenium preparation (sodium selenite) alone group, and control group. The route of administration was oral administration, and the period of administration was 28 days.

The number of administration was once a day. The dosage was 10 ml/kg body weight and was administrated using an oral zonde.

The dosages of each group are shown below.

TABLE 1

| Test group | Dosage | Concentration | Dose (ml/kg) | Number of animals |
|---|---|---|---|---|
| Control | 0 | 0 | 10 | 8 |
| Selenium preparation (sodium selenite) | 150 μg/kg | 15 μg/ml | 10 | 8 |
| Zinc preparation (polaprezinc) | 45.2 mg/kg | 4.52 mg/ml | 10 | 8 |
| Zinc preparation (polaprezinc) + Selenium preparation (sodium selenite) | 45.2 mg/kg + 150 μg/kg | 4.52 mg/ml + 15 μg/ml | 10 | 8 |

Blood was collected from the heart under ether anesthesia at the end of administration. The obtained serum was divisionally injected into a tube. It was euthanized by exsanguination after blood sampling and the photograph of the extracted liver was taken. For all necropsied animals, treatment was made to divide the liver into four respective lobes (right/left medial lobe, left lateral lobe, right lobe, caudate lobe), wherein especially the left lateral lobe was treated for three parts taking two each of its six equally divided parts, and the tissue image was analyzed.

The evaluation for non-alcoholic fatty liver disease (NAFLD) and/or non-alcoholic steatohepatitis (NASH) improvement was evaluated by the following items.

(1) HE stained tissue
(2) F4/80 antibody (macrophage) stained tissue
(3) Oil-Red-O stained (intracellular lipid droplets) tissue
(4) Liver weight and the change in liver weight to body weight
(5) The change in ALT
(6) The change in serum ferritin level
(7) The change in MDA (malondialdehyde)
(8) The change in hepatic TG (hepatic triglyceride)
(9) The change in MCP-1 (monocyte chemotactic promoting factor)
(10) The change in TNF-alpha (tumor necrosis factor)
(11) The change in IFN-gamma (interferon-gamma)
(12) The change in the hepatic fibrosis area ratio
(13) The activity change by NAS (steatosis, lobular inflammation, ballooning degeneration and NAS)

(Tissue Image of the Liver)

FIG. 1 is a figure showing the HE stained tissue image of the four groups. In FIG. 1, as the result of HE stain, the reduction in number of adipocytes and the size of the adipocytes was observed, and balloon-like degeneration of the centrilobular hepatocyte and fibrosis around the cell were suppressed in the group of the combination drug of zinc preparation (polaprezinc) and selenium preparation (sodium selenite) compared with the other groups. Improvement in the tissue image of deposition of macrovesicular fat in the liver tissue, balloon-like hypertrophy (ballooning) of the hepatocyte, infiltration of the inflammatory cell, and the like, which are the features of non-alcoholic fatty liver disease (NAFLD) became clear by the combination drug of zinc preparation (polaprezinc) and selenium preparation (sodium selenite).

(Tissue Image of the Liver)

FIG. 2-1 is a figure showing the F4/80 (macrophage) stained tissue image of the four groups.

FIG. 2-2 is a figure showing the F4/80 (macrophage) stained tissue image of the four groups.

In FIG. 2-1 and FIG. 2-2, F4/80 is one of an antigen that expresses specifically in a macrophage which constantly expresses in a Kupffer cell which is a macrophage existing in liver sinusoids and the like, its expression level is numerous, and is controlled by the physiological condition of the cell. The zinc preparation (polaprezinc) alone and selenium preparation (sodium selenite) alone also suppresses the expression level significantly compared with the control, but the expression level is significantly decreased in the group of the combination drug of zinc preparation (polaprezinc) and selenium preparation (sodium selenite) compared with the three groups of the control group, the zinc preparation (polaprezinc) alone, and the selenium preparation (sodium selenite) alone. The histological structure configured by the fatty degenerated hepatocyte and macrophage becomes the factor of inflammation and fibrosis, and appears proportionately to the severity of non-alcoholic fatty liver disease (NAFLD) and/or non-alcoholic steatohepatitis (NASH) (nonpatent literature 8). The decrease of macrophage means reducing severity of non-alcoholic fatty liver disease (NAFLD) and/or non-alcoholic steatohepatitis (NASH). The decrease of antigen expression level means the decrease of macrophage, and the suppression of the activity of Kupffer cell which is a macrophage existing in liver sinusoids became clear.

Nonpatent Literature 8

Michiko Itoh et. al, "Hepatic Crown-Like Structure: A Unique Histological Feature in Non-Alcoholic Steatohepatitis in Mice and Humans", PLoS ONE 2013.8.12 e82163

(Tissue Image of the Liver)

FIG. 3 is a figure showing the Oil-Red-O stained (intracellular lipid droplets) tissue image of the four groups.

In FIG. 3, since Oil-Red-O dissolves into the solvent of the cellular lipid upon contacting the adipocytes and develops color, it is conducted to ascertain the differentiation from a preadipocyte to an adipocyte. The lipid in fat is stained red, and the nucleus is stained blue. It became clear that the stained area of the lipid in fat is small, and that the differentiation of the adipocyte from a preadipocyte to an adipocyte is less in the group of the combination drug of zinc preparation (polaprezinc) and selenium preparation (sodium selenite) compared with the three groups of the control group, the zinc preparation (polaprezinc) alone group, and the selenium preparation (sodium selenite) alone group.

(Liver Weight)

FIG. 4 is a figure showing liver weight.

In FIG. 4, liver weight increases since fat is accumulated in liver in non-alcoholic fatty liver disease (NAFLD) and/or non-alcoholic steatohepatitis (NASH). In liver weight, the group of the combination drug of zinc preparation (polaprezinc) and selenium preparation (sodium selenite) was 1,239.9 mg after administration, the control group was 1,467 mg after administration, the zinc preparation (polaprezinc) alone group was 1,389 mg after administration, and the selenium preparation (sodium selenite) alone group was 1,385.2 mg after administration. The combination drug of zinc preparation (polaprezinc) and selenium preparation (sodium selenite) significantly decreased liver weight in contrast with the control group and the zinc preparation (polaprezinc) alone group, and showed a decrease tendency in contrast with the selenium preparation (sodium selenite) alone group.

FIG. 5 is a figure showing the data of the weight ratio of liver to body.

In the weight ratio of liver to body shown in FIG. 5, the group of the combination drug of zinc preparation (polaprezinc) and selenium preparation (sodium selenite) was 6.82% after administration, the control group was 7.71% after administration, the zinc preparation (polaprezinc) alone group was 7.49% after administration, and the selenium preparation (sodium selenite) alone group was 7.43% after administration. The group of the combination drug of zinc preparation (polaprezinc) and selenium preparation (sodium selenite) significantly declined in contrast with the control group, and showed a declining tendency in contrast with the zinc preparation (polaprezinc) alone group and the selenium preparation (sodium selenite) alone group.

(The change in the degree of inflammation)

FIG. 6 is a figure showing the data of ALT.

In FIG. 6, for the serum ALT level, the group of the combination drug of zinc preparation (polaprezinc) and selenium preparation (sodium selenite) was 37.8 IU/L after administration, the control group was 74.2 IU/L after administration, the zinc preparation (polaprezinc) alone group was 58.8 IU/L after administration, and the selenium preparation (sodium selenite) alone group was 54.6 IU/L after administration. The group of the combination drug of zinc preparation (polaprezinc) and selenium preparation (sodium selenite) significantly declined ALT, which shows the degree of inflammation of liver, compared with the three groups of the control group, the zinc preparation (polaprezinc) alone group, and the selenium preparation (sodium selenite) alone group.

FIG. 7 is a figure showing the data of serum ferritin.

In FIG. 7, the serum ferritin level reflects the stored iron content in the body. Therefore, in case the serum ferritin level is in high level, it significantly correlates with the iron accumulation in liver and is considered to be iron overload. When the iron storage organ, liver, is damaged, the serum ferritin level elevates by the deviation of iron from liver, and the organ is damaged by the active oxygen causable by iron overload. It is reported that iron overload further relates significantly as a factor which contributes to enlargement in NAS (NAFLD activity score) and the advance of hepatic fibrosis (nonpatent literature 9). Therefore, to protect the organ by improving iron overload becomes important. The group of the combination drug of zinc preparation (polaprezinc) and selenium preparation (sodium selenite) was 3,448.8 ng/ml, which significantly decreased the serum ferritin level compared with the three groups of the control group of 7,207 ng/ml, the zinc preparation (polaprezinc) alone group of 5,740 ng/ml, and the selenium preparation (sodium selenite) alone group of 5,251 ng/ml.

Nonpatent Literature 9

Kris V Kowdley et. al, "Elevated serum ferritin is an independent predictor of histologic severity and advanced fibrosis among patients with nonalcoholic fatty liver disease", Hepatology 2012.55(1):77-85

FIG. 8 is a figure showing the data of MDA (malondialdehyde).

In FIG. 8, MDA is measured as a marker of oxidative stress. Wherein oxidative stress is an important factor in NASH progression, the group of the combination drug of zinc preparation (polaprezinc) and selenium preparation (sodium selenite) significantly declined the lipid peroxide concentration which is an oxidative stress marker compared with the three groups of the control group, the zinc preparation (polaprezinc) alone group, and the selenium preparation (sodium selenite) alone group. The group of the combination drug of zinc preparation (polaprezinc) and selenium preparation (sodium selenite) was 37.8 IU/L after administration, the control group was 74.2 IU/L after administration, the zinc preparation (polaprezinc) alone group was 58.8 IU/L after administration, and the selenium preparation (sodium selenite) alone group was 54.6 IU/L after administration.

FIG. 9 is a figure showing the data of hepatic TG (hepatic triglyceride).

In FIG. 9, non-alcoholic fatty liver disease (NAFLD) is what is led to the damage of liver by the deposition of triglyceride to the hepatocyte and its advance progresses to non-alcoholic steatohepatitis (NASH). The group of the combination drug of zinc preparation (polaprezinc) and selenium preparation (sodium selenite) significantly decreased intrahepatic triglyceride and suppressed the deposition of triglyceride to liver compared with the three groups of the control group, the zinc preparation (polaprezinc) alone group, and the selenium preparation (sodium selenite) alone group. The group of the combination drug of zinc preparation (polaprezinc) and selenium preparation (sodium selenite) was 41.1 mg/dl after administration, the control group was 78.7 mg/dl after administration, the zinc preparation (polaprezinc) alone group was 64.2 mg/dl after administration, and the selenium preparation (sodium selenite) alone group was 57.3 mg/dl after administration.

FIG. 10 is a figure showing the data of MCP-1 (monocyte chemotactic protein-1).

In FIG. 10, the production of inflammatory cytokine such as MCP-1 increases in the pathological condition of NASH and is reported that MCP-1 progresses NASH through its receptor (CCR2) (nonpatent literature 10). It was shown that the group of the combination drug of zinc preparation (polaprezinc) and selenium preparation (sodium selenite) suppress the production of MCP-1 and demonstrates the protective action on liver function. The group of the combination drug of zinc preparation (polaprezinc) and selenium preparation (sodium selenite) was 2.4 after administration, the control group was 4.2 after administration, the zinc preparation (polaprezinc) alone group was 3.3 after administration, and the selenium preparation (sodium selenite) alone group was 3.2 after administration. The group of the combination drug of zinc preparation (polaprezinc) and selenium preparation (sodium selenite) significantly declined MCP-1 in contrast with the control group, and showed a declining tendency in contrast with the zinc preparation (polaprezinc) alone group and the selenium preparation (sodium selenite) alone group.

Nonpatent Literature 10

Kouichi Miura et. al, "Hepatic recruitment of macrophages promotes nonalcoholic steatohepatitis through CCR2", Am J Physiol Gastrointest Liver Physiol 2012.302: 1310-1321

FIG. 11 is a figure showing the data of TNF-alpha (tumor necrosis factor-alpha).

In FIG. 11, TNF-alpha is one of an adipocytokine (biologically active agent) secreted from adipocytes which have action to suppress the agency of glucose in muscles, adipose tissues, and liver. It increases when obese and heightens the risk of diabetes and arteriosclerosis. It became clear that it is a protein that induces inflammation and that TNF-alpha induces acute inflammation and chronic inflammation as a pro-inflammatory cytokine. The Kupffer cell which is a macrophage of liver activates by degeneration of the hepatocyte, the lapse into suicide, and the necroinflammation being caused in the process of fat accumulating in the hepatocyte, and furthermore, in obesity or chronic drinkers, the intestinal flora changes and the increased endotoxin reaches the liver from the intestine, and leads to the activation of the Kupffer cell. An inflammatory cytokine such as TNF-alpha emigrates from this activated cell, the inflammatory response advances, and progresses to fibrosis around the hepatocyte. The Score showing the degree of inflammation was 8.42 in the group of the combination drug of zinc preparation (polaprezinc) and selenium preparation (sodium selenite), which significantly suppressed the inflammation attributed to TNF-alpha compared with the control group of 16.29 and the selenium preparation (sodium selenite) alone group of 13.23, and showed a suppressing tendency compared with the zinc preparation (polaprezinc) alone group of 12.80.

FIG. 12 is a figure showing the data of IFN-gamma (interferon-gamma).

In FIG. 12, the Kupffer cell which is a macrophage of the hepatocyte is activated by IFN-gamma stimulation. IFN-gamma is involved in inflammatory cytokine production of TNF-alpha and the like, and advances the inflammation of the hepatocyte. Therefore, suppression of IFN-gamma contributes to suppression of inflammation and fibrosis of the hepatocyte. The Score showing the degree of inflammation was 4.20 in the group of the combination drug of zinc preparation (polaprezinc) and selenium preparation (sodium selenite), 10.69 in the control group, 8.02 in the selenium preparation (sodium selenite) alone group, 7.95 in the zinc preparation (polaprezinc) alone group, and the group of the combination drug of zinc preparation (polaprezinc) and selenium preparation (sodium selenite) significantly suppressed the inflammation attributed to IFN-gamma in contrast with the control group and the selenium preparation (sodium selenite) alone group, and showed a suppressing tendency in contrast with the zinc preparation (polaprezinc) alone group.

FIG. 13 is a figure showing the data of hepatic fibrosis area ratio.

In FIG. 13, hepatic fibrosis do not necessarily advance in non-alcoholic fatty liver disease (NAFLD) and/or non-alcoholic steatohepatitis (NASH). It is reported that, in non-alcoholic fatty liver disease (NAFLD), 37% advanced in hepatic fibrosis, 34% were stable, and 29% returned to normal (nonpatent literature 1). For the hepatic fibrosis area ratio, the group of the combination drug of zinc preparation (polaprezinc) and selenium preparation (sodium selenite) was 0.81%, and showed 1.47% in the control group, 1.16% in the zinc preparation group (polaprezinc) alone group, and 1.18% in the selenium preparation (sodium selenite) alone group. The group of the combination drug of zinc preparation (polaprezinc) and selenium preparation (sodium selenite) significantly decreased the hepatic fibrosis area ratio compared with the control group and the selenium preparation (sodium selenite) alone group, and showed a tendency of decrease compared with zinc preparation (polaprezinc).

NAS (NAFLD activity score) is used to evaluate non-alcoholic fatty liver disease (NAFLD). NAS is advocated by Nonalcoholic•Steato•hepatitis•Clinical•Research•Network (nonpatent literature 2). NAS correlates with clinical diagnosis, shows the activity in full score of 8, being regarded as NASH for the most part with the score not less than 5, as mixed with suspected NASH and non-NASH with the score of 3 or 4, and as non-NASH for the most part with the score less than 3. The activity of NAS is evaluated by putting the three of steatosis, lobular inflammation, and Ballooning degeneration into scores. It is shown in full score of 8 in total, score of 0 to 3 for steatosis and lobular inflammation, and score of 0 to 2 for hepatic Ballooning degeneration. Steatosis, lobular inflammation, hepatic Ballooning degeneration, and NAS (NAFLD activity score) was compared and examined for the four groups, the group of the combination drug of zinc preparation (polaprezinc) and selenium preparation (sodium selenite), the control group, the zinc preparation (polaprezinc) alone group, and the selenium preparation (sodium selenite) alone group. Hepatic Ballooning especially becomes the key for the diagnosis of non-alcoholic fatty liver disease (NAFLD) and its suppression is suggested to be important (nonpatent literature 11).

Nonpatent Literature 11

Christi A Matteoni et. al, "Nonalcoholic Fatty Liver Disease: A Spectrum of Clinical and Pathological Severity", Gastroenterology 1999.116.1413-1419

FIG. 14 is a figure showing the data of hepatic ballooning.

In FIG. 14, the group of the combination drug of zinc preparation (polaprezinc) and selenium preparation (sodium selenite) was 0.38, which significantly suppressed hepatic ballooning compared with the control group of 1.85, the zinc preparation (polaprezinc) alone group of 1.38, and the selenium preparation (sodium selenite) alone group of 1.23. Non-alcoholic fatty liver disease (NAFLD) is classified into type-1 to type-4 depending on the progression, and hepatic ballooning is first observed in type-3 and type-4, which is diagnosed as non-alcoholic steatohepatitis (NASH). Since progression to cirrhosis and liver disease-related death increases significantly in type-3 and type-4 compared with type-1 and type-2 (nonpatent literature 11), hepatic ballooning is considered more important to progression. Thus, it is important to suppress the advance of hepatic ballooning. The decrease of progression to cirrhosis and liver disease-related death of non-alcoholic fatty liver disease (NAFLD) and/or non-alcoholic steatohepatitis (NASH) is expected with the combination drug of zinc preparation (polaprezinc) and selenium preparation (sodium selenite) by significantly suppressing hepatic ballooning.

FIG. 15 is a figure showing the data of lobular inflammation (hepatic lobular inflammation).

In FIG. 15, the group of the combination drug of zinc preparation (polaprezinc) and selenium preparation (sodium selenite) of 0.85 significantly suppressed lobular inflammation compared with the control group of 2.23. A suppressing tendency was seen compared with the zinc preparation (polaprezinc) alone group of 1.38 and the selenium preparation (sodium selenite) alone group of 1.46.

FIG. 16 is a figure showing the data of steatosis (hepatic steatosis).

In FIG. 16, the group of the combination drug of zinc preparation (polaprezinc) and selenium preparation (sodium selenite) of 0.54 significantly suppressed (intrahepatic) steatosis compared with the control group of 1.54. In contrast with the zinc preparation (polaprezinc) alone group of 0.85 and the selenium preparation (sodium selenite) alone group of 0.85, a suppressing tendency was seen.

FIG. 17 is a figure showing the data of NAS (NAFLD activity score).

In FIG. 17, the group of the combination drug of zinc preparation (polaprezinc) and selenium preparation (sodium selenite) was 1.77, the control group was 5.62, the zinc preparation (polaprezinc) alone group was 3.62, and the selenium preparation (sodium selenite) alone group was 3.54. Among the four groups, NAS of the group of the combination drug of zinc preparation (polaprezinc) and selenium preparation (sodium selenite) was in significantly low level compared with the three groups of the control group, the zinc preparation (polaprezinc) alone group, and the selenium preparation (sodium selenite) alone group.

Although the zinc preparation (polaprezinc) and the selenium preparation (sodium selenite) alone group also significantly declined NAS (NAFLD activity score) compared with the control group, the group of the combination drug of zinc preparation (polaprezinc) and selenium preparation (sodium selenite) improved NAS (NAFLD activity score) more significantly compared with the zinc preparation (polaprezinc) alone group and the selenium preparation (sodium selenite) alone group. Balloon-like degeneration of the hepatocyte (hepatic Ballooning) especially becomes the key for the diagnosis in non-alcoholic fatty liver disease (NAFLD) and/or non-alcoholic steatohepatitis (NASH) and its suppression is suggested to be important (nonpatent literature 11).

Also from this viewpoint, as a non-alcoholic fatty liver disease (NAFLD) and/or non-alcoholic steatohepatitis (NASH) therapeutic agent, the combination drug of zinc preparation (polaprezinc) and selenium preparation (sodium selenite) proves to be a more significant and effective non-alcoholic fatty liver disease (NAFLD) and/or non-alcoholic steatohepatitis (NASH) therapeutic agent compared with the respective independent preparation of zinc preparation (polaprezinc) and selenium preparation (sodium selenite).

INDUSTRIAL APPLICABILITY

The present invention may combine in addition to the combination drug for treatment and prevention use of non-alcoholic fatty liver disease (NAFLD) and/or non-alcoholic steatohepatitis (NASH), and/or hepatic fatty degeneration, combination drugs for treatment of diseases related or associated with this or one kind or plural kinds of other active substances, and is applied to the pharmaceutical formulation and health food for use in treatment and prevention of non-alcoholic fatty liver disease (NAFLD) and/or non-alcoholic steatohepatitis (NASH).

What is claimed is:

1. A method for treating non-alcoholic steatohepatitis (NASH), the method comprising administering to a subject in need thereof a therapeutically effective amount of a pharmaceutical composition, wherein:
    the pharmaceutical composition comprises polaprezinc as zinc preparation and sodium selenite as selenium preparation, and
    the polaprezinc as zinc preparation is administered at a dose of 45.2 mg/kg per day and the sodium selenite as selenium preparation is administered at a dose of 150 µg/kg per day.

* * * * *